(12) United States Patent
Wang et al.

(10) Patent No.: US 11,761,032 B2
(45) Date of Patent: Sep. 19, 2023

(54) METHODS AND DEVICES FOR PERFORMING REAL TIME DIGITAL PCR

(71) Applicants: Yan Wang, San Diego, CA (US); Cory McCluskey, San Diego, CA (US)

(72) Inventors: Yan Wang, San Diego, CA (US); Cory McCluskey, San Diego, CA (US)

( * ) Notice: Subject to any disclaimer, the term of this patent is extended or adjusted under 35 U.S.C. 154(b) by 255 days.

(21) Appl. No.: 16/504,065

(22) Filed: Jul. 5, 2019

(65) Prior Publication Data

US 2019/0345546 A1 Nov. 14, 2019

Related U.S. Application Data

(63) Continuation-in-part of application No. 15/901,900, filed on Feb. 22, 2018, now abandoned.

(60) Provisional application No. 62/470,211, filed on Mar. 11, 2017.

(51) Int. Cl.
*C12Q 1/68* (2018.01)
*C12Q 1/6851* (2018.01)
*C12Q 1/6825* (2018.01)
*B01L 7/00* (2006.01)
*B01L 3/00* (2006.01)

(52) U.S. Cl.
CPC .......... *C12Q 1/6851* (2013.01); *B01L 3/5027* (2013.01); *B01L 7/52* (2013.01); *C12Q 1/6825* (2013.01)

(58) Field of Classification Search
CPC .. C12Q 1/6851; C12Q 1/6825; C12Q 1/6806; C12Q 1/686; C12Q 2565/62; B01L 7/52; B01L 3/5027; B01L 2200/027; B01L 2300/0819
See application file for complete search history.

(56) References Cited

U.S. PATENT DOCUMENTS

| | | | | |
|---|---|---|---|---|
| 5,475,610 A * | 12/1995 | Atwood | .......... | B01L 7/52 700/269 |
| 9,457,351 B2 * | 10/2016 | Tan | .......... | G01N 21/6452 |
| 2006/0281183 A1 * | 12/2006 | Sun | .......... | G01N 35/00871 436/43 |
| 2009/0139311 A1 * | 6/2009 | Lehto | .......... | B01L 3/502 73/61.72 |
| 2011/0057117 A1 * | 3/2011 | Fawcett | .......... | G01N 21/6452 250/458.1 |
| 2011/0306055 A1 * | 12/2011 | Haince | .......... | G01N 33/57419 435/6.14 |
| 2012/0214160 A1 * | 8/2012 | Deng | .......... | C12Q 1/6886 435/6.11 |
| 2014/0024559 A1 * | 1/2014 | Unger | .......... | G02B 21/36 506/12 |
| 2014/0171341 A1 * | 6/2014 | Jouvenot | .......... | G16B 5/00 506/12 |
| 2016/0101418 A1 * | 4/2016 | Lee | .......... | C12Q 2563/107 506/9 |

FOREIGN PATENT DOCUMENTS

| CN | 105092543 A | * | 11/2015 | | |
|---|---|---|---|---|---|
| RU | 2595373 C1 | * | 8/2016 | | |
| WO | WO-2017007954 A1 | * | 1/2017 | .......... | C12Q 1/686 |

OTHER PUBLICATIONS

Kiss et al. "High-Throughput Quantitative Polymerase Chain Reaction in Picoliter Droplets", 2008, Analytical Chemistry, 80, 8975-8981 (Year: 2008).*
Li et al. "Picoliter Well Array Chip-Based Digital Recombinase Polymerase Amplification for", Apr. 13, 2016, PLOS One, 11, 4, e0153359. (Year: 2016).*
English translation of RU2595373C1. (Year: 2016).*
English translation of CN105092543A. (Year: 2015).*
Snith et al. (J of Cell Biol 2015, 209(4):609-619) (Year: 2015).*
Zhu et al. (Lab Chip, 2014, vol. 14, p. 1176-1185) (Year: 2014).*

* cited by examiner

*Primary Examiner* — Stephanie K Mummert
(74) *Attorney, Agent, or Firm* — Lili Chen

(57) ABSTRACT

Disclosed are devices that can perform multiple independent digital PCRs with real-time monitoring capability. The device comprises multiple PCR mini-reactors thermally coupled with its own temperature control element, a detection unit, and a motor for moving the PCR mini-reactors or the detection unit. The real-time digital PCR device can simultaneously perform multiple digital PCRs, generate amplification curves of thousands and millions of individual PCR processes, evaluate binary readouts based on the kinetic properties of individual amplification curves, and identify different target sequences based on the amplification curves. Methods of using the real-time digital PCR device to detect target nucleic acids and count circulating tumor cells are also disclosed.

9 Claims, 11 Drawing Sheets

METHODS AND DEVICES FOR PERFORMING REAL TIME DIGITAL PCR

CROSS-REFERENCE TO RELATED APPLICATIONS

This application is a continuation-in-part of U.S. patent application Ser. No. 15/901,900, filed Feb. 22, 2018, which claims the benefit of U.S. provisional patent application No. 62/470,211, filed Mar. 11, 2017, the content of both applications are incorporated by reference herein.

FIELD OF THE INVENTION

This invention relates to methods and devices for detection of target nucleic acids or target cells, especially relates to methods and devices for using real-time digital PCR for detecting target nucleic acids and target cells.

BACKGROUND OF THE INVENTION

Polymerase chain reaction (PCR) is a method that uses a DNA polymerase and DNA polymerization reaction to generate thousands and millions of copies of a specific nucleic acid. It generally undergoes thermal cycles at different temperatures to repeatedly perform denaturing of double-stranded DNA, annealing of primers to target DNA sequences, and extending of primers to generate copies of the target sequence. PCR is an indispensable technique in molecular biology that is widely used to detect, identify, obtain and quantitate a DNA/RNA sequence of interest.

Quantitative PCR, also called real-time qPCR, is a technique to quantitate the amount of a target sequence by monitoring the generation of the target sequence during the PCR amplification cycles. The production of the target sequence is monitored in real-time either by a non-specific, fluorescent dyes that intercalate with any double stranded DNAs or by sequence-specific DNA probes that emit a detectable signal upon hybridization to a complimentary sequence. During a qPCR, the DNA-based fluorescence is measured at any time during the PCR cycles. The quantity of the target sequence is determined based on $C_t$, the threshold cycle number when the detected fluorescence level exceeds a threshold that is significantly above the background noise level. The relative quantification of gene expression can be determined by comparing the $C_t$ of RNA/DNA from the target gene to the Ct of RNA/DNA from a house-keeping reference gene in the same sample. The absolute quantification is difficult and is usually based on creation of a standard curve with known DNA dilutions. Factors such as the variance of PCR amplification efficiency and non-exponential amplification can affect the accuracy of quantitative results and limit its ability to discriminate small fold-differences of gene quantities.

Digital PCR (dPCR) is a refinement of PCR technologies that allows absolute quantification of nucleic acid strands. The dPCR improves upon the conventional PCR by partitioning one PCR reaction into many small individual PCR reactions such that each small reaction on average contains no more than one target nucleic acid molecule. Each small reaction approximately contains either 1 or 0 target nucleic acid molecule and gives a positive or negative binary readout at the end of PCR amplification. The fraction of positive readouts is determined and the absolute fraction of the target gene can be calculated based on Poisson statistical model. dPCR determines the absolute amount of the target gene by counting the actual target molecules, which does not depend on the exponential amplification cycle number and comparison to a reference gene for quantification of the initial amount. By using massive amount of partitions, dPCR can be used to detect finer fold-differences than that of qPCR.

Since dPCR only concerns positive or negative readout from each reaction, the dPCR is often performed by detecting the end point reaction products. However, the end point measurement lacks the real-time kinetic information about each reaction, which can provide valuable information for mechanistic investigation, assay optimization, and evaluation of false positives. Additionally, using the real-time amplification information in PCR detection can increase the dynamic range of PCR detection and enable detection of multiple target sequences using the same fluorescent probe. The present invention provides a real-time digital PCR device with multiple independently-controlled mini-PCR reactors that can perform multiple independent dPCR amplifications with real-time monitoring.

SUMMARY OF THE INVENTION

The present invention provides a device that can perform multiple independent digital PCRs with real-time monitoring capability. The device comprises multiple PCR mini-reactors thermally coupled with its own temperature control element, a detection unit, and a motorized mechanism for moving the PCR mini-reactors or the detection unit. The real-time digital PCR device can simultaneously perform multiple dPCRs, generate amplification curves of individual PCR process, evaluate binary readouts based on the amplification curves, and identify different target sequences based on properties of the amplification curves.

The present invention provides a device for performing real-time digital PCR, comprising: a) at least one PCR mini-reactor wherein the PCR mini-reactor comprises a PCR microchip thermally coupled to a temperature control element, wherein the thermal cycle of each PCR mini-reactor is independently controlled by its respective temperature control element; b) a detection unit wherein the detection unit can be programmed to take images at defined intervals; c) a motorized platform for moving the PCR mini-reactor to the right position for taking an image of the PCR microchip of the PCR mini-reactor; and d) a computing unit connected to the detection unit, the motorized platform, and the temperature control element of each PCR mini-reactor for controlling and coordinating the operation of these parts. In another alternative embodiment, the position of the PCR mini-reactors are fixed and the detection unit is attached to a motor so that it can be programmed to move to the right position of a PCR mini-reactor to take a timely picture of the respective PCR microchip in the PCR mini-reactor.

In one embodiment, the PCR microchip is a microfluidic plate with more than 100, 1000, 10000 or 100000 chambers.

In one embodiment, the PCR microchip comprises microfluidic channels that can make microdroplets form a single layer configuration. The PCR microchip is further connected to a micro-droplet generator which can inject microdroplets into the microfluidic channels of the PCR microchip.

In one embodiment, the temperature control element comprises a heating element, a temperature sensor and a cooling element. The temperature control element is connected to a heater control Printed Circuit Board (PCB) which is further controlled by the computing unit (e.g. in the form of a computer, a tablet or a mobile device). In one embodiment, the heating element comprises a bottom heater with built-in heat sinks and bottom temperature sensors. The PCR microchip sits directly on the bottom heater. The heat sinks comprise cooling fins used for rapid cooling during the thermocycles. Cooling fans can be built underneath the bottom heaters for rapid cooling. In one embodiment, the temperature control element further comprises an actuatable top heater assembly that can be moved out of the way to allow for imaging. The top heater assembly comprises a retractable top heater integrated with top temperature sensors.

In one embodiment, the detection unit comprises a light source, optical filters, a fluorescence microscope and a camera. The fluorescence microscope is a high resolution, wide-field microscope. In one embodiment, mini-PCR reactors are fixed in position and the detection unit can be driven by a motor to move to a desired position for taking a picture of a particular mini-PCR reactor. In another embodiment, the detection unit are fixed in position and the mini-PCR reactors can be moved by a motor to the right position for picture-taking. The motor is connected to a system control PCB which is connected and controlled by the computing unit.

In another embodiment, the present invention provides a method for detecting a plurality of target sequences in a sample using a real-time digital PCR device described herein, comprising: a) partitioning a mixture of the sample and PCR reagents into many small individual reaction volumes in the PCR microchip of the real-time digital PCR device such that more than 50% of the reaction volumes contain no more than one target sequence, wherein the mixture comprises primer pairs for amplification of target sequences and sequence-specific reporter probes for detection of target sequences; b) performing multiplexed real-time quantitative PCR to amplify a plurality of target sequences in each reaction volume; c) recording an amplification curve for each reaction volume during the PCR amplification using the detection unit of the device; and d) determining the presence of individual target sequence in each reaction volume based on the amplification curve of the reaction volume.

In one embodiment, the sequence-specific reporter probes are coupled to the same fluorescent group, and concentrations of the primers and the sequence-specific reporter probes are different for each target sequences which results in different plateau fluorescence intensities for each target sequences, and the detection of a particular target sequence is based on the plateau fluorescence intensity.

In one embodiment, the PCR amplification for different target sequence has different threshold cycle numbers (Ct) and the detection of a particular target sequence is based on the Ct.

In some embodiment, the detection of a target sequence is based on the plateau fluorescence intensity and the Ct of the amplification curve of the target sequence.

In some embodiment, the mixture of the sample and PCR reagents is partitioned into many small individual reaction volumes such that more than 50% of the reaction volumes contain no more than one nucleic acid sequence.

In one embodiment, the present invention provides a method for counting circulating tumor cells expressing a tumor-specific gene or having a tumor-specific genomic sequence in a cell sample using a device described herein, comprising: a) partitioning a mixture of RT-PCR reagents and a cell sample enriched with circulating tumor cells into many small individual reaction volumes in the PCR microchip such that more than 50% of the reaction volumes contain no more than one circulating tumor cell, wherein the mixture comprises primers for amplification of a plurality of tumor-specific sequences and a plurality of sequence-specific reporter probes for detection of the plurality of tumor-specific sequences; b) performing multiplexed real-time quantitative RT-PCR to amplify the plurality of tumor-specific sequences in each reaction volume; c) recording an amplification curve for each reaction volume during the PCR amplification; d) counting the number of reaction volumes with positive signals based on the amplification curve of the reaction volume; and e) determining the fraction of circulating tumor cells in the cell sample based on the fraction of reaction volumes with positive signals. The reaction volumes with positive signals are identified as reaction volumes with a circulating tumor cell.

In some embodiment, concentrations of the primers and the sequence-specific reporter are different for each tumor-specific sequence which results in different plateau fluorescence intensities for each tumor-specific sequence, and the detection of a circulating tumor cell having a particular tumor-specific sequence is based on the plateau fluorescence intensity.

In some embodiment, the PCR amplification for each tumor-specific sequence has a different Ct and the detection of a circulating tumor cell having a particular tumor-specific sequence is based on the Ct.

In some embodiment, the detection of a circulating tumor cell having a particular tumor-specific sequence is based on the plateau fluorescence intensity and the Ct.

In some embodiment, the mixture of PCR reagents and the cell sample is partitioned into many small individual reaction volumes in the PCR microchip such that more than 50% of the reaction volumes contain no more than one single cell.

In some embodiment, the reaction volumes identified as having circulating tumor cells can be retrieved and used for further analysis. For example, the microdroplets having positive fluorescent signals are identified as ones with circulating tumor cells and the microdroplets with circulating tumor cells can be sorted by a droplet sorter.

DETAILED DESCRIPTION

Figure 1:
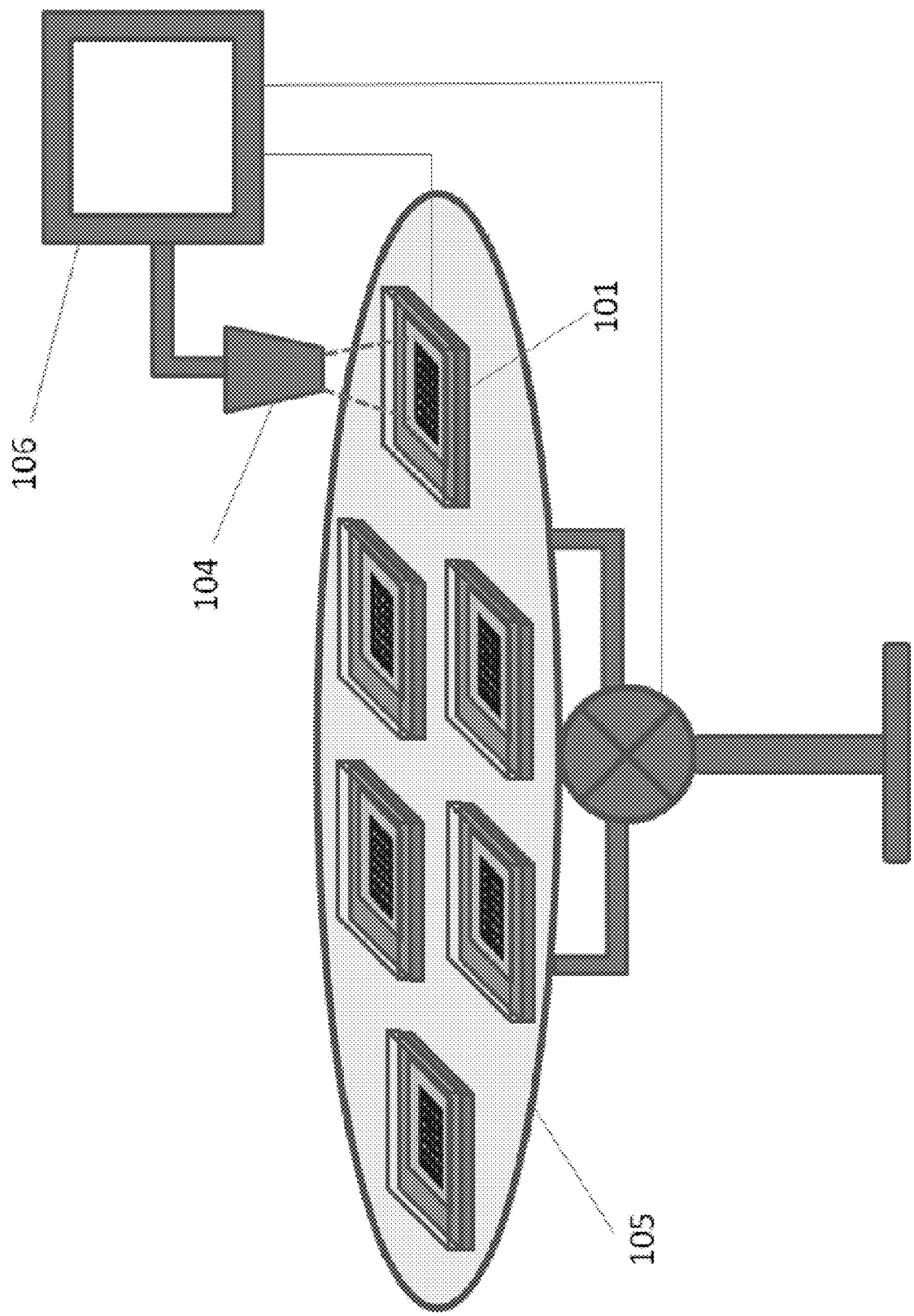
FIG. 1. Components of a real-time digital PCR device. a PCR mini-reactor <101>, a detection unit <104>, a motorized platform <105>, and a computing unit <106>.
Figure 2:
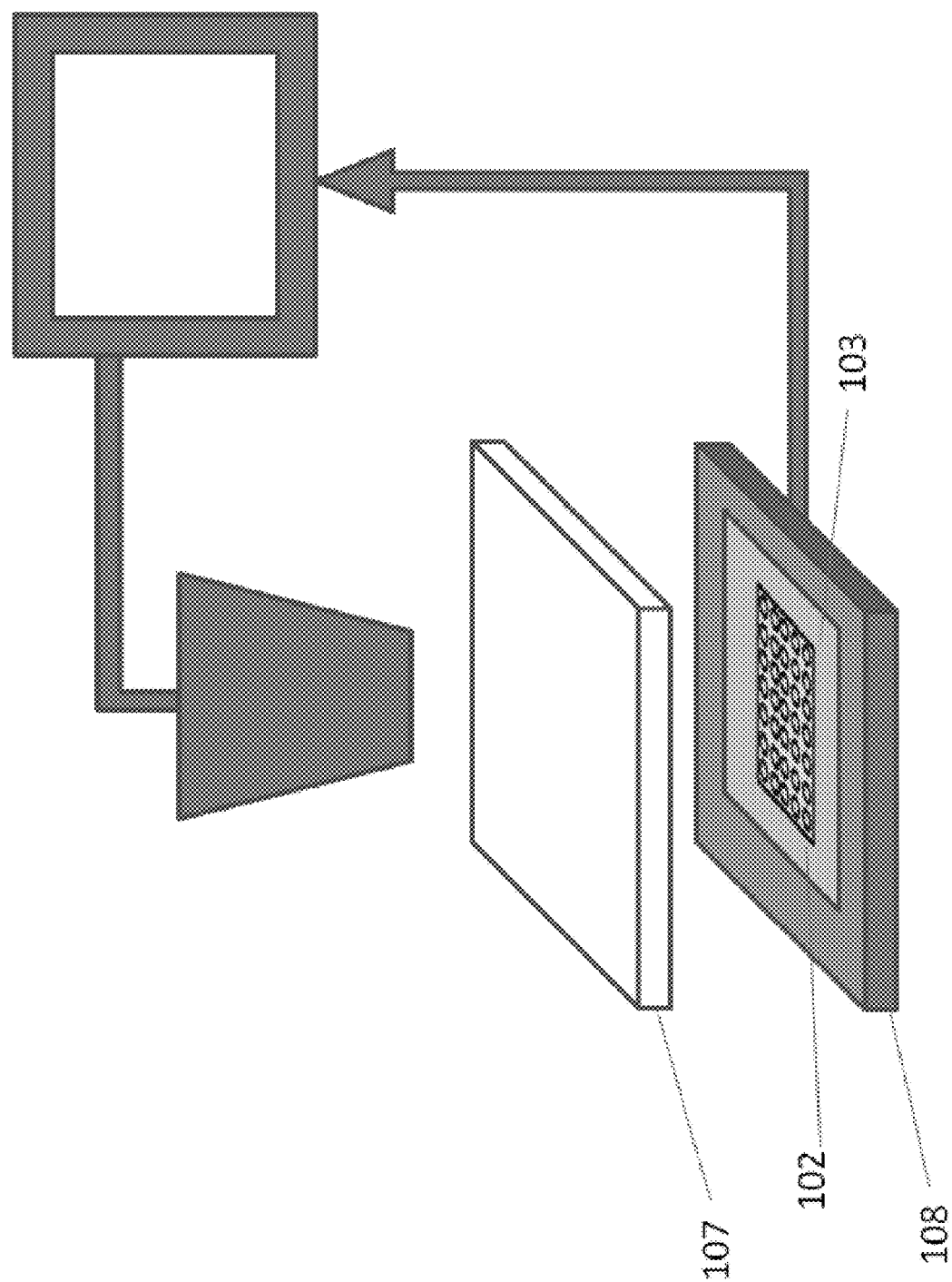
FIG. 2. Components of a PCR mini-reactor. a PCR microchip <102>, a temperature control element <103>, a transparent cover plate <107>, and a bottom plate integrated with the temperature control element <108>.

Definitions: Unless otherwise defined, all technical and scientific terms used herein have the same meaning as commonly understood by one of the ordinary skill in the art to which this invention belongs.

The term "a" and "an" and "the" as used to describe the invention, should be construed to cover both the singular and the plural, unless explicitly indicated otherwise, or clearly contradicted by context. Similarly, plural terms as used to describe the invention, for example, nucleic acids, nucleotides and DNAs, should also be construed to cover both the plural and the singular, unless indicated otherwise, or clearly contradicted by context.

The term "digital PCR" or "dPCR", as used herein, refers to a polymerase chain reaction technology that uses binary outputs of many PCR amplifications to make absolute quantification of target nucleic acids. dPCR starts by partitioning a sample into many small individual compartments such that each compartment on average contains no more than one target element, and amplification reactions are then performed to determine the presence or absence of the target element in each compartment. The fraction of compartments with the target element (p) is used to calculate the actual fraction of the target element in the sample (τ) based on Poisson statistic model where $\tau=-\ln(1-p)$. The target element can be RNA/DNA sequence of interest or specific cell type (e.g. circulating tumor cell, or cells infected with viruses). Specific cell types are identified by the presence of marker nucleotide sequences specific for the particular cell type. For detection of specific cell type, there can be more than one copy of marker sequences in each compartment. In some embodiment, the detection of the presence of the marker sequence in a compartment gives a positive readout for the compartment. In another embodiment, the detection of an expression level of marker sequences in a compartment higher than the average background level gives a positive readout for the compartment.

The term "real-time digital PCR", as used herein refers to a digital PCR in which generation of the PCR product is monitored during the PCR amplification cycles. In a real-time digital PCR, the temporal data of the PCR process in each compartment can be used in evaluation of the binary output and discrimination of different target elements.

The term "circulating tumor cells", as used herein, refers to tumor cells that are dissociated from the original tumor, enter into the vasculature or lymphatic system and are carried around the body by circulation. These cells carry tumor cell specific expression profiles and tumor-specific genotype, and can become the seed cells to grow into metastatic tumors. The circulating tumor cells can be identified by their expression of tumor specific genes and lack of expression of blood cell specific markers such as CD45.

The term "tumor-specific sequences", as used herein, refers to nucleic acid sequences including RNA or DNA sequences that have higher representation in cancerous cells as compared to normal cells, especially normal blood cells or lymphatic cells. Tumor specific RNA sequences may be RNA transcripts that are expressed in one or more types of cancer cells, but have very low or no expression in normal blood or lymphatic cells. The tumor specific genes that are only expressed in tumor cells with no detectable expression in normal blood or lymphatic cells are referred as "cancer-only marker genes". Tumor specific DNA sequences are DNA sequences that are only present in cancer cells or over-represented in cancer cells, including, for example, cancer-specific gene fusion sequences and gene sequences with copy number multiplication in cancer cells. The tumor specific sequences may be over-represented in a specific cancer type or many different cancer types. The tumor specific sequences related to a specific cancer type (e.g. breast cancer) can be selected as a cancer type specific set and used to detect tumor cells related to the particular cancer type. The tumor-specific sequences that are expressed in many different cancer types can be used as pan-cancer markers for detection of cancer occurrence.

The term "tumor specific primers", as used herein, refers to PCR primers that are designed to amplify tumor specific sequences in polymerase chain reactions. The tumor specific primers are designed such that they specifically amplify respective tumor specific sequences, but not other sequences present in normal cells. For example, the tumor specific primers for amplification of tumor specific RNA transcripts are designed to produce amplicons spanning multiple exons so that they will not amplify genomic sequences of the corresponding genes. The tumor specific primers for amplification of a gene fusion sequence are designed to produce an amplicon across the fusion junction so that the gene sequence to be amplified exists only in cancer cells.

Most commercially available digital PCR machines measure the end-point PCR products after PCR amplifications are completed. However, the temporal data of PCR cycles that can provide valuable information for analysis of dPCR readouts are unavailable in these end-point digital PCRs. The present invention provides a device that can perform multiple independent digital PCRs with real-time monitoring capability. The device comprises multiple PCR mini-reactors, each coupled with its own temperature control element, a detection unit, and a motorized platform for holding and moving the PCR mini-reactors. The real-time digital PCR device can simultaneously perform multiple digital PCRs, generate amplification curves of thousands and millions of individual PCR processes, evaluate binary readouts based on the amplification curves, and identify different target sequences based on the amplification curves.

The present invention provides a device for performing real-time digital PCR, comprising: a) at least one PCR mini-reactor <101> wherein the PCR mini-reactor comprises a PCR microchip <102> thermally coupled to a temperature control element <103>, wherein thermal cycling of each PCR mini-reactor is independently controlled by its respective temperature control element; b) a detection unit <104> wherein the detection unit can be programmed to take images at defined intervals; c) a motorized platform <105> for holding more than one PCR mini-reactors that can be programmed to move one of the PCR mini-reactors to the right position to be taken an image by the detection unit; and d) a computing unit <106> connected to the detection unit, the motorized platform, and the temperature control elements of the PCR mini-reactors.

In one embodiment, the PCR microchip is a microfluidic plate with more than 100, 1000, 10000, 100000 or 1000000 chambers. The microfluidic plate can be fabricated from silicon or glass substrate. Polymers, such as polydimethylsiloxane (PDMS), polycarbonate (PC) and polymethylmethacrylate (PMMA) can also be utilized as alternative substrates. The suitable substrate should have good thermal conductivity and be able to withstand sustained high temperature associated with PCR. The inner surface of chambers should be treated to become hydrophilic using reagents such as $SiO_2$, bovine serum albumin (BSA), polyethylene glycol (PEG), or silanizing agents (for example 3-glycidoxypropyl trimethoxysilane, dichlorodimethylsilane, Sigmacoat® or trimethylchlorosilane) (Zhang, C. and Xing, D. Nucleic Acids Res. 2007; 35(13): 4223-4237). The outside surface of chambers can be treated to be hydrophobic so as to prevent cross-contamination between chambers. To load the mixture of the sample and PCR reagents, a scraping blade with a piece of a soft silica gel at an end can be used to scrap the mixture into the microchip. After loading the sample, the microchip needs to be covered with a layer of mineral oil to prevent evaporation during the PCR process. A transparent cover plate <107> with good optical property is used to close the top of the microchip. The cover plate can be made of glass or transparent plastic material with good optical property. For example, commercially available digital PCR chips (Life technologies, Carlsbad, Calif.) are well suited to be used as microchips of the invention.

Figure 3:
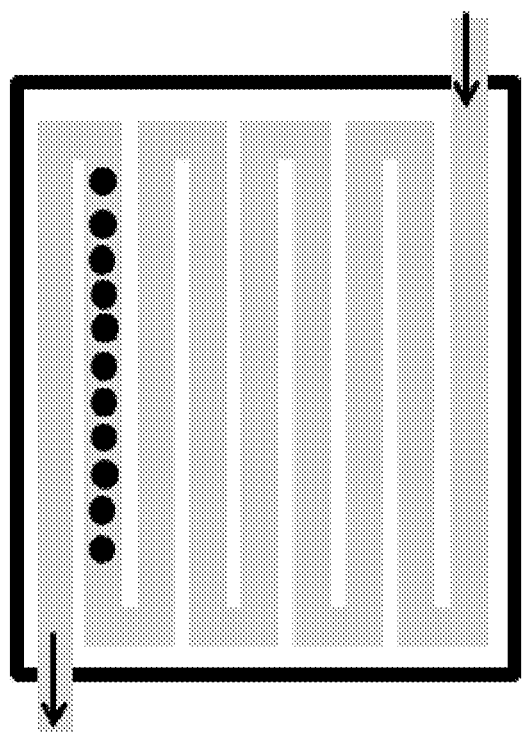
FIG. 3. Examples of PCR microchips for microdroplets. A, a PCR microchip with a flat channel; B, a PCR microchip with a U-shaped channel.
Figure 3:
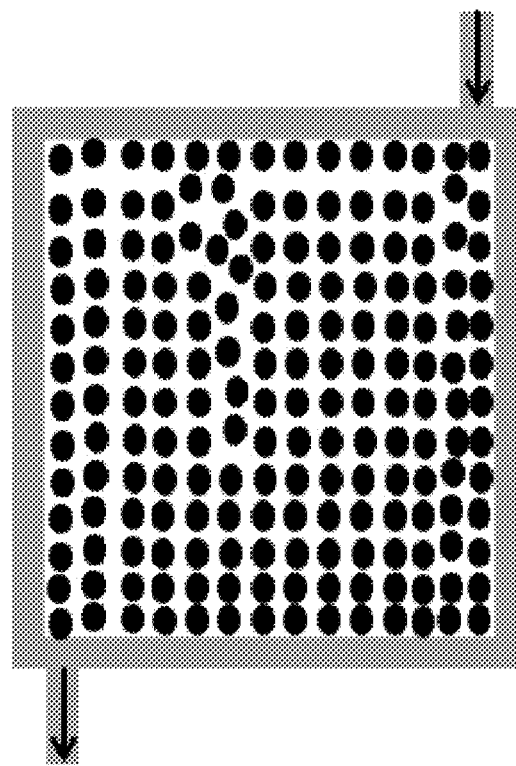

In one embodiment, the PCR microchip comprises microfluidic channels that can make microdroplets form a single layer configuration, which is suitable for taking pictures of the microdroplets during the PCR amplification. For example, the inner height of the microfluidic channels are made to be 1.2-1.8 folds of the average diameter of microdroplets so that only a single layer of microdroplets can be formed inside the microfluidic channels. The inside of the microfluidic channel can be a flat open space (FIG. 3A) or U-shaped tubes (FIG. 3B). The PCR microchip has an inlet and an outlet for loading and extracting microdroplets, respectively. The PCR microchip can be connected to a microdroplet generator which can encapsulate a DNA sample and PCR reagents into thousands and millions of microdroplets and inject the microdroplets into the microfluidic channels of the PCR microchip. At least one side of the PCR microchip is made of transparent materials so that real-time images of the microdroplets can be taken during the PCR process.

In one embodiment, the temperature control element comprises a heating element, a temperature sensor and a cooling element, which is connected and controlled by a heater control circuitry. The heating element and the temperature sensor should be in tight thermal contact with the PCR microchip. The heating element can be, for example, a thin film electrode heater, a block heater or a Peltier device that can perform heating and cooling as needed. The heater control circuitry uses the temperature sensor to measure the current temperature of the PCR microchip, compare the current temperature with the target temperature and make needed adjustment to reach the target temperature. The methods that can be used to make temperature control elements for PCR microchips are known in the art (Koo C, et al. PLoS ONE 2013; 8(12): e82704. doi:10.1371/journal.pone.0082704 and Miralles, V. et al. Diagnostics (Basel). 2013 March; 3(1): 33-67). The temperature control element can be made as an integrated part of a PCR microchip or as an independent part that is thermally coupled with the PCR microchip during the PCR process. The temperature control element is connected to a computing unit (e.g. a computer) and the control of the thermal cycles of each PCR microchip is operated through the computing unit. Each PCR mini-reactor has its own temperature control element and can independently perform PCR amplification under its own thermal cycle. This design adds flexibility to the device, allowing parallel operation of multiple PCRs with different thermal cycles and easy manipulation for monitoring multiple real-time PCR amplifications.

In one embodiment, the detection unit comprises a light source, optical filters, a fluorescence microscope and a camera. The fluorescence microscope is a wide-field high resolution microscope. The camera used in the invention can be, for example, a CCD camera.

In some embodiment, the computing unit serves as the central control of the dPCR device that controls the detection unit, the motorized platform and the temperature control elements of the PCR mini-reactors and coordinates the action of different parts to make a whole unit. The computing unit can be, for example, a control console or a computer. It can be used to set thermal cycle parameters for each PCR mini-reactor, to control the motorized platform to move PCR mini-reactors, control the detection unit to take pictures and store data acquired from the detection camera. Each mini-reactor can have different start time, thermal cycling temperatures, and heating times. The temporal parameters for the movement of the motorized platform and the picture-taking can be set to match to that of each mini-reactor. The computing unit can control operation parameters to coordinate the thermal cycle timing of each mini-reactor, the movement of motorized platform, and the picture-taking of the detection unit so that pictures can be taken at defined time point of each thermal cycle for each mini-reactor.

For example, it takes 3 seconds to take a picture of a PCR microchip to move a mini-reactor. In order to take a picture at the exact end of each PCR cycle for each PCR mini-reactor, the PCR mini-reactors can be programmed to start its PCR cycle with a sequential 3 seconds delay and the detection unit can be programmed to sequentially take a picture at the end of each PCR cycle for respective PCR mini-reactor. Table 1 shows an example for setting the temporal parameters for one PCR cycle of a 8-reactor dPCR device that a picture is taken at the end of the PCR cycle for each mini-reactor. Temporal parameters for more PCR cycles can be set up similarly.

TABLE 1

An example of temporal parameters for a 8-reactor dPCR

| Mini-reactor No. | PCR cycle time | Cycle start time | Picture-taking time |
| --- | --- | --- | --- |
| 1 | 60 sec | 0 sec | 57-60 sec |
| 2 | 60 sec | 3 sec | 60-63 sec |
| 3 | 60 sec | 6 sec | 63-66 sec |
| 4 | 60 sec | 9 sec | 66-69 sec |
| 5 | 60 sec | 12 sec | 69-72 sec |
| 6 | 60 sec | 15 sec | 72-75 sec |
| 7 | 60 sec | 18 sec | 75-78 sec |
| 8 | 60 sec | 21 sec | 78-81 sec |

Figure 6:
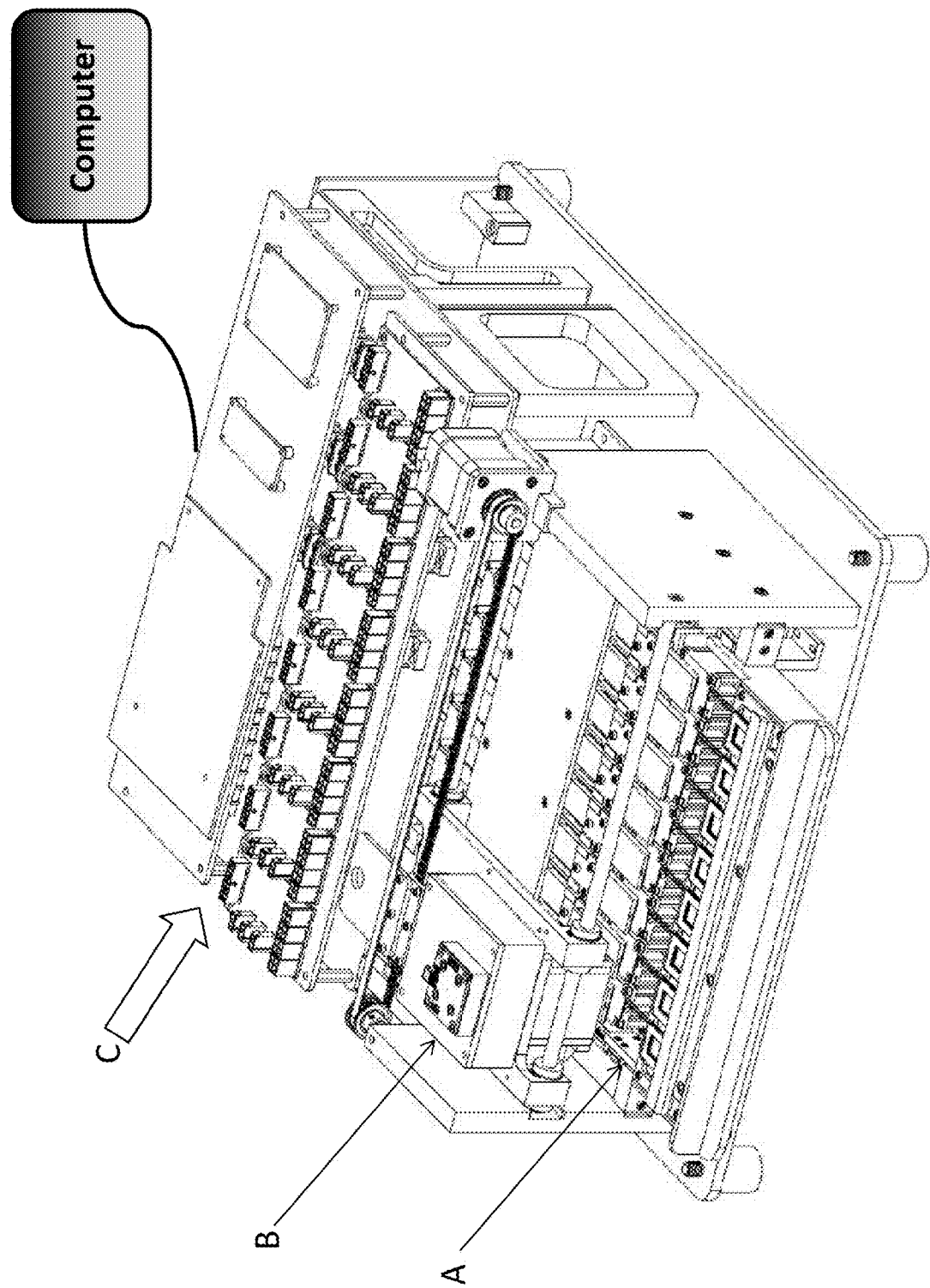
FIG. 6. An isometric view of an assembled digital PCR embodiment, including A) PCR mini-reactors comprising PCR microchips thermally coupled to respective temperature control element; B) a motor-driven detection unit; and C) a computing unit with control PBCAs connected to a computer.
Figure 7:
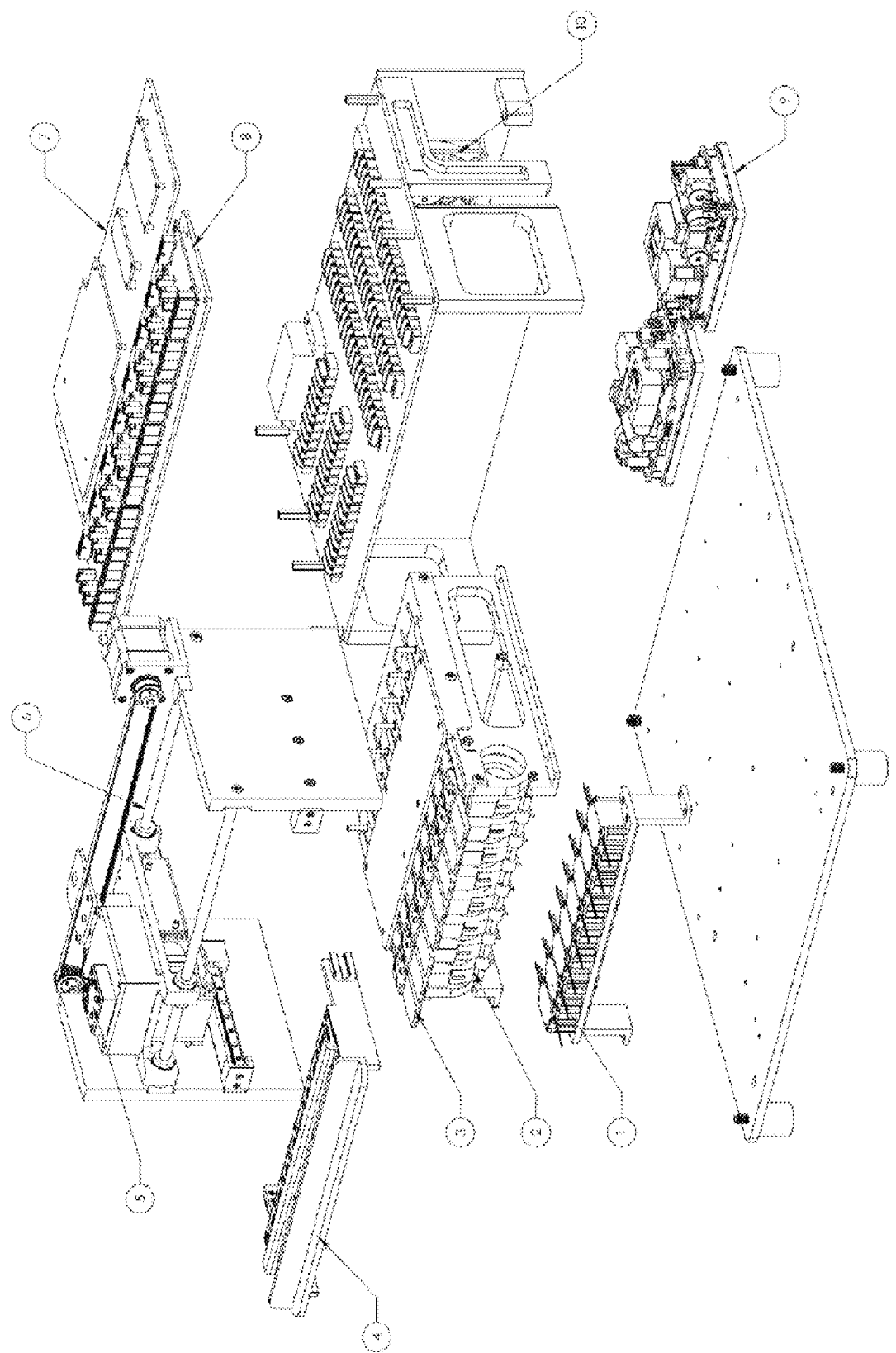
FIG. 7. An exploded view of a digital PCR assembly, including bottom heaters with built in heat sinks for cooling (1); bottom heater cooling fans as part of the bottom heater sub-assembly (2); actuatable top heaters which can individually be moved out of the way to allow for imaging (3); a PCR Chip holding drawer assembly (4); a camera with a filter wheel (5); a motor driven optics assembly with top heater actuator (6); system control PCBAs to control various device functions including motors, camera, and switches (7); heater control PCBAs to control the heaters, fans, and corresponding sensors (8); power supplies (9); and power supply cooling fans (10).
Figure 8:
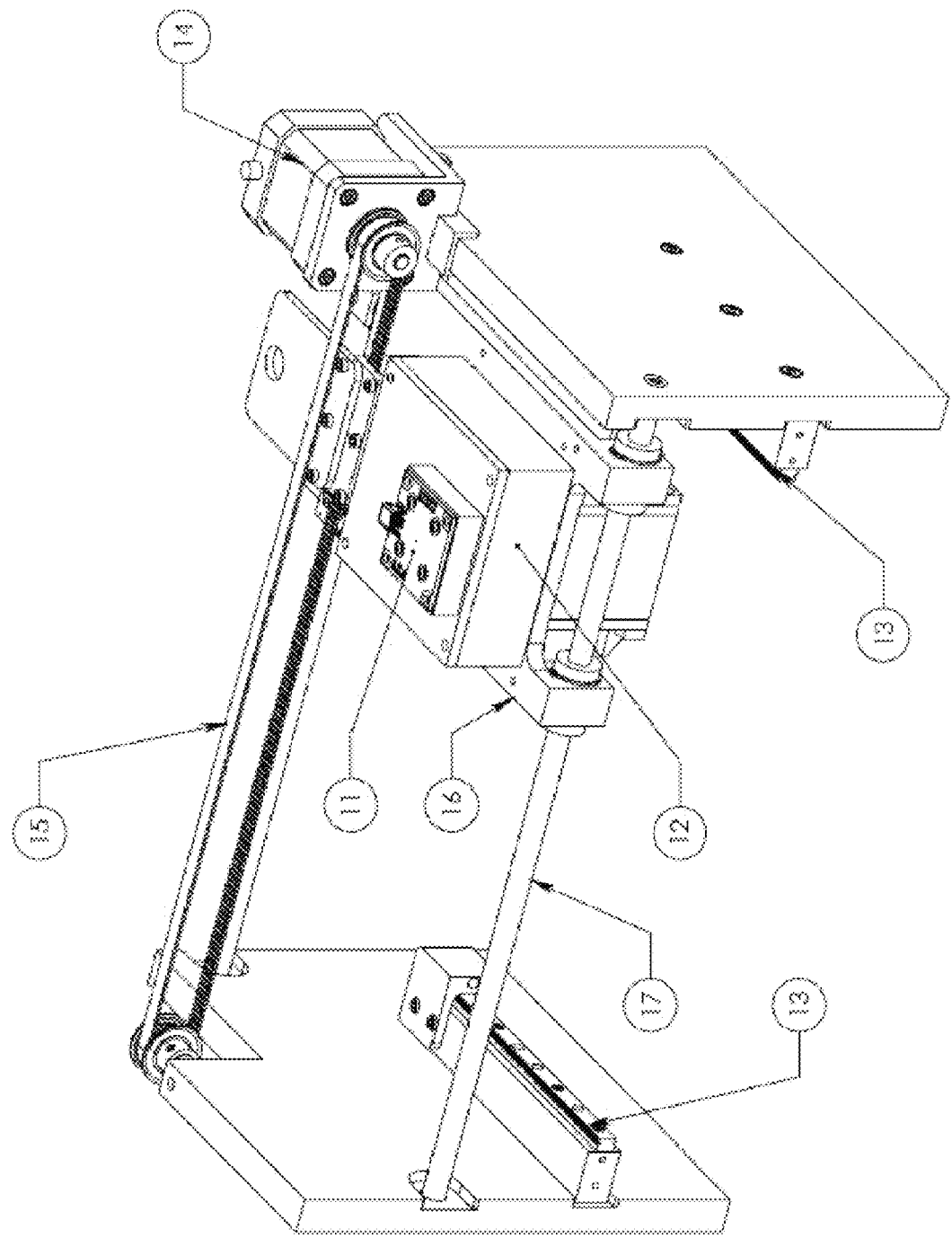
FIG. 8. An isometric view of a detection unit, including a camera (11), a filter wheel (12), drawer rails (13), an optics motor (14), a belt drive (15), a camera carriage (16), and rails for camera carriage (17).
Figure 9:
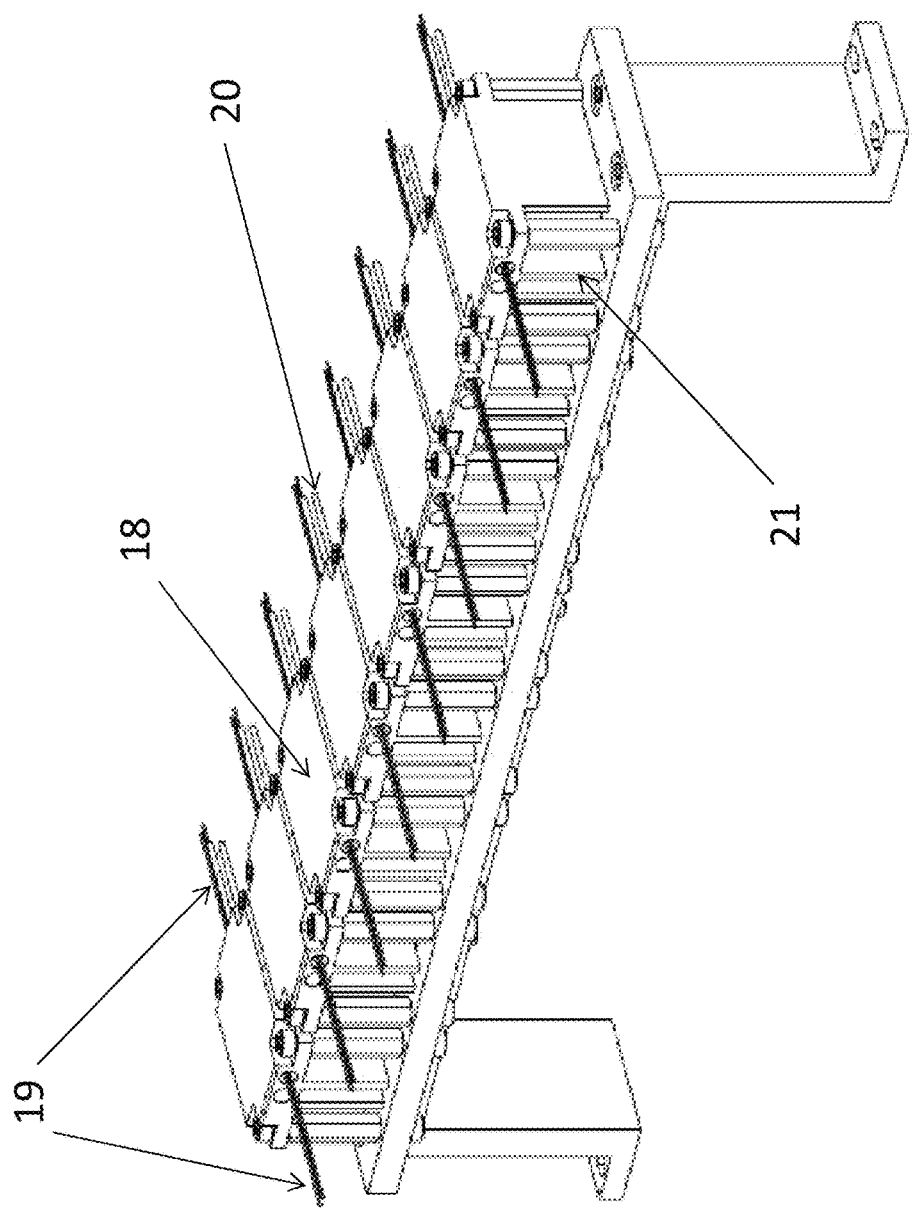
FIG. 9. An isometric view of a bottom heater assembly, including bottom heaters (18), temperature sensors (19), heating rods (20) and cooling fins (21).

In one embodiment, the present invention provides a real-time digital PCR machine as shown in FIG. 6, comprising PCR mini-reactors having PCR microchips thermally coupled with respective temperature control element (FIG. 6A), a motor-driven detection unit (FIG. 6B), and a computing unit comprising PBCAs connected to a computer (FIG. 6C).

Figure 10:
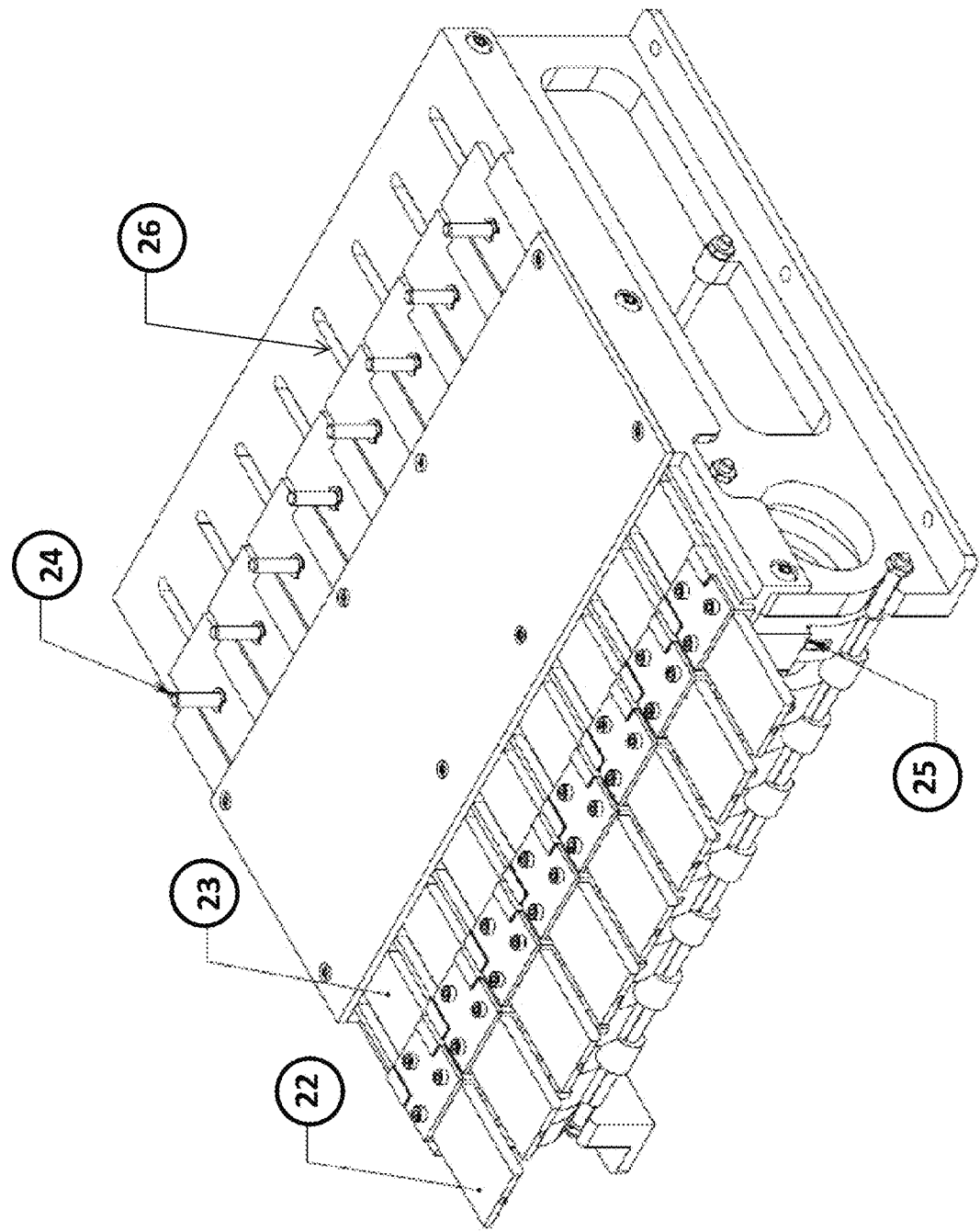
FIG. 10. An isometric view of a top heater assembly, including top heaters (22), sliders (23), actuator pins (24), cooling fans for cooling the bottom heater (25), and return springs (26).
Figure 11:
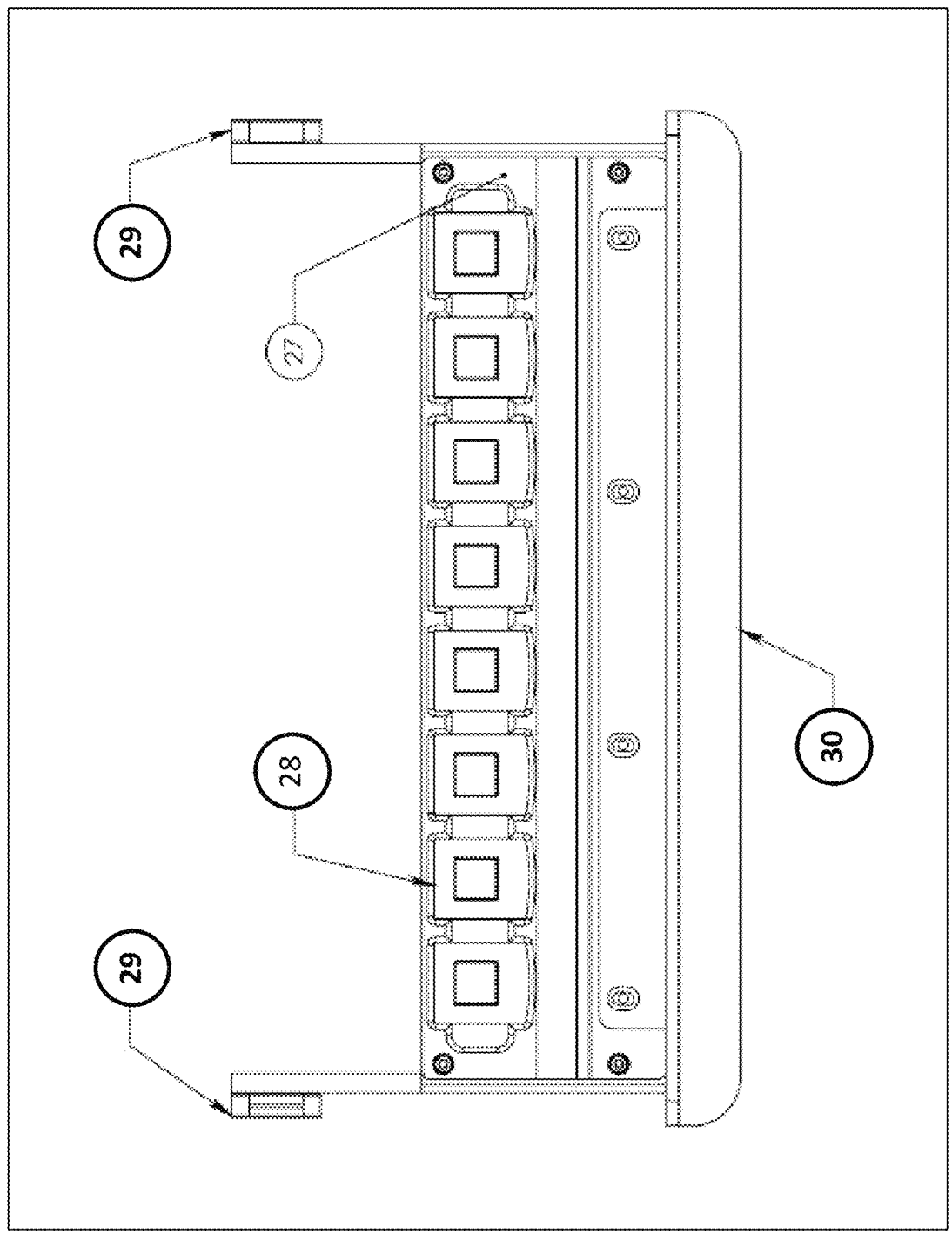
FIG. 11. A top view of a drawer assembly with PCR chips, including a chip plate (27), PCR chips (28), drawer handles (29), and a carriage (30).

The exemplary device has eight PCR mini-reactors, each comprising a PCR microchip <28> thermally coupled to its own individual temperature control element. This permits each PCR mini-reactor to have its own thermal cycling profile, enabling performance of up to eight simultaneous PCR amplifications under different thermal profiles. The temperature control element comprises an actuatable top heater <22> integrated with top temperature sensors and a bottom heater <18> integrated with bottom temperature sensors <19> and cooling fins <21>. The top heater can be set to a fixed temperature and be retracted to the back to allow for image capturing. The top heater is connected via a slider <23> to a motor-driven actuator that can open and close the top heater. The motor <14> can move the detection unit to the PCR mini-reactor of interest and control the open and close of its top heater. The action of the motor is centrally controlled by a master control software on the computing unit (e.g. a computer). The temperature of the top heater is usually kept at a fixed high temperature (e.g. 70° C.) without changing during PCR thermal cycles. The function of the heated top heater is mainly for the purpose to prevent heat loss from the top surface of the microchip, while the temperature of the reaction solution during the thermal cycle is controlled by the bottom heater. The top heater has one or more temperature sensors but no cooling mechanism. Alternatively, the top heater can be equipped with a heat sink and have a changing temperature profile during the PCR process. The bottom heater has built-in temperature sensors and a cooling mechanism such as cooling fins, which are designed for quick cooling of the bottom heater using forced air from a cooling fan <25> underneath. The cooling fan built as a part of the bottom heater assembly (FIG. 10) is used to generate forced air to quickly cool down the cooling fins of the bottom heater. Other cooling mechanism can be used for this purpose includes, but not limited to, Peltier devices and liquid-based cooling devices. A good heater suitable for use in the invention should have fast heating and cooling rate and even heat distribution, including, but not limited to, metal block heaters, thin film heaters and Peltier devices. A customarily made thin film heater can achieve up to 175° C./s heating rate and 125° C./s cooling rate can be used to greatly reduce the reaction time for PCR (Nucleic Acids Res. 2006; 34:e77). For cost-effective development of heating device, commercially available thin film heaters with a heating rate of 6.5° C. or higher and Peltier devices are alternative choices. The exemplary device employs an aluminum block heater with temperature sensors integrated inside the heater. The block heater has resistive heating element inserted inside the block. To increase the evenness of heat distribution, the heating element can be more evenly inserted into the heating block. For example, multiple heating elements or U-shaped heating elements can be integrated into the heating block. Flat resistive heating element and plastic film can also be bonded to the aluminum block to better spread out the heat. Many electrical temperature sensors that can convert temperature signals into electronic signals can be used as the temperature sensors in the invention, including, but not limited to, thermistors, thermocouples and resistance thermometers. During the performance of a PCR, PCR microchips are inserted into a chip holding drawer assembly (FIG. 11) and are closely engaged with top and bottom heaters when the chip holding drawer is inserted into the dPCR machine.

In one embodiment, the detection unit comprises a LED light source with illumination bandpass filter, a dichroic mirror, a filter wheel and a digital camera. The detection unit can be moved by a motor to a desired position over a PCR mini-reactor of interest for picture-taking. The motor also controls the actuator which is connected to the top heater via a slider to move the top heater out of the way to allow for capturing an image. After capturing the image, the top heater is returned to the original position by the motor. When taking an image, a beam of LED light passes through the first filter which passes wavelengths of light in a specific bandwidth, removing the wavelengths of light that are the same as those of the fluorescent dye emission lights. The wavelengths of light passed the first filter is shorter than the wavelengths of light passed through the dichroic mirror and the filters on the filter wheel. The dichroic mirror reflects the LED source light to shine on the whole field of the PCR microchip. The fluorescent lights emitted from the fluorescent dyes pass through the dichroic mirror and the filter wheel, and are received by the digital camera. The dichroic mirror is designed such that it reflects short wavelength excitation lights and transmits long wavelength emission lights. The filter wheel is used to switch between different emission filters to selectively prioritize the wavelengths of light coming from fluorescent dyes of interest. Using the detection unit, real-time full field images of each microchip are captured during the process of digital PCR and are used for retrieval of real-time kinetic information of each compartmentalized reaction.

The computing unit comprises system control PCBAs, heater control PCBAs and a control computer. The system PCBAs control various device such as motors, camera, and switches. The heater PCBAs control the heaters, cooling fans, and corresponding sensors. The system PCBAs and the heater PCBAs are connected to the control computer which has a master software for providing full control of the instrument components. The thermal cycling parameters of each temperature control element can be individually set and configured in the software before start of any program. The motor can be programmed to move the detection unit to the position of the desired mini-reactor and open/close the top heater to allow for picture-taking at any pre-defined time points. The start of a PCR program for each mini-reactor does not need to be the same. In order to take a picture at the same time point of the thermal cycle of each mini-reactor, it is preferable to start the PCR thermal cycle with a sequential delay as shown above (Table 1). Configuration for the camera is provided in the software for defining parameters such as picture-taking time, exposure time, camera gain, region of interest, and framerate etc. The configuration of emission filter wheels is provided for selecting the desired combination of emission filters to obtain good quality images.

The software also provides a full suite of tools for image processing and data analysis. Many methods can be implemented in the software to calibrate the full-field images and reduce imaging noises, including, but not limited to, flat field calibration, chromatic filter calibration, dark field subtraction, median averaging of multiples images, background subtraction, etc. With these calibration techniques implemented, the image quality can be greatly improved. Additionally, ROX, as a passive and inert dye, can be added to each reaction well to act as an internal reference dye to normalize fluorescent signal and correct well-to-well optical variation. Because the camera is constantly moving among different PCR mini-reactors, alignment of images of the same PCR mini-reactor is important for proper analysis of the imaging data. The image alignment is achieved by finding similar features in the images and applying homography techniques to align the features. The wells/chambers in a PCR microchip are identified by thresholding and contour size estimation.

With real-time monitoring capacity of digital PCR process, the kinetic information for each compartmentalized reaction can be obtained and used for evaluation of digital readouts and optimization of digital efficiency. Methods for evaluating digital readouts include using maximum amplification value, threshold amplification value and the shape of the amplification curve. Compared to end-point PCR, real-time PCR allows for using the kinetic information of each well's readout to better determine the real positives. The points can be evaluated by comparing the shape and height of the real-time PCR amplification curve against expected values, or against the values of other wells in the microchips. For example, some wells may appear bright throughout the PCR process, which can be excluded as positive readouts in real-time PCRs, but will appear as false positive results in end-point PCRs. The increase of fluorescent signals in some wells may appear too early compared to the expected cycle time or those of the peer wells. These wells should be excluded from positive results. Some wells may have too many zero value readouts, which is an indication of abnormality in the readout signals and these wells should be excluded from positive results. The ratio of the last and the initial cycle readout can be set a threshold for selecting positive wells. The value difference between the final and the initial readout can be used as another criteria for evaluating positive vs. negative result. The positive selection criteria may also set an acceptable level that the readout of the last cycle can be dropped from the maximum readout.

In one embodiment, the present invention provides a method for detecting a plurality of target sequences in a sample using a real-time digital PCR device described herein, comprising: a) partitioning a mixture of the sample and PCR reagents into many small individual reaction volumes in the PCR microchip of the real-time digital PCR device such that more than 50% of the reaction volumes contain no more than one target sequence, wherein the mixture comprises primer pairs are used for amplification of target sequences and sequence-specific reporter probes are used for detection of target sequences; b) performing multiplexed real-time quantitative PCR to amplify a plurality of target sequences in each reaction volume; c) recording an amplification curve for each reaction volume during the PCR amplification using the detection unit of the device; and d) determining the presence of individual target sequence in each reaction volume based on the amplification curve of the reaction volume. One advantage of the real-time digital PCR is that it can use the shape of the amplification curve to evaluate if a positive fluorescent signal is true or false signal. This method can effectively exclude the false positive signals from non-specific amplification and increase the quantification accuracy of the dPCR.

In some embodiment, the sequence-specific reporter probes for different target sequences are linked to different fluorophores. The partitions with different target sequence can be identified based on the type of fluorescence in the partition. However, the number of available fluorophores is limited and different fluorophores often have overlapping spectrums, making it difficult to discriminate among different fluorescent signals. The most commonly available fluorophores used in the digital PCR detection are only two types. It is therefore important to develop means for discriminating different targets using the same fluorophore. Using the characteristics of the amplification curve to discriminate different target sequences is one of the solutions.

Figure 4:
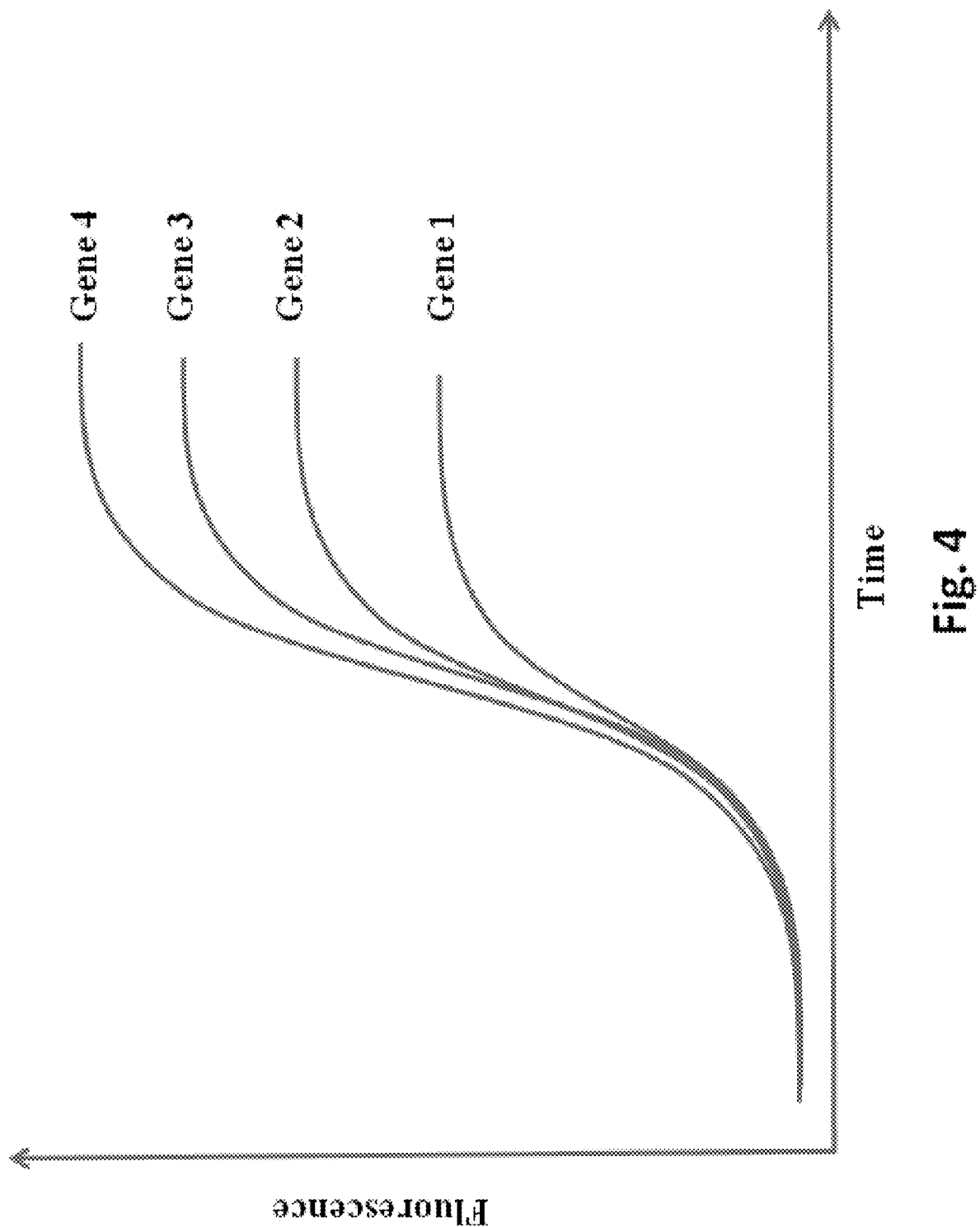
FIG. 4. dPCR amplification curves of four genes with different plateaus.

In some embodiment, concentrations of the primers and the sequence-specific reporter probes are different for each target sequence which results in different plateau fluorescence intensities for each target sequence, and the detection of a target sequence is based on the plateau fluorescence intensity. The plateau fluorescence intensity is directly related to the amount of primers and sequence-specific reporter probes. For example, FIG. 4 shows four genes each having a different plateau fluorescence intensity. Amplification curves can be used to calculate the plateau fluorescence intensity with better resolution than those of the end point measurements, thus providing a better way to discriminate signals from different target sequences.

Figure 5:
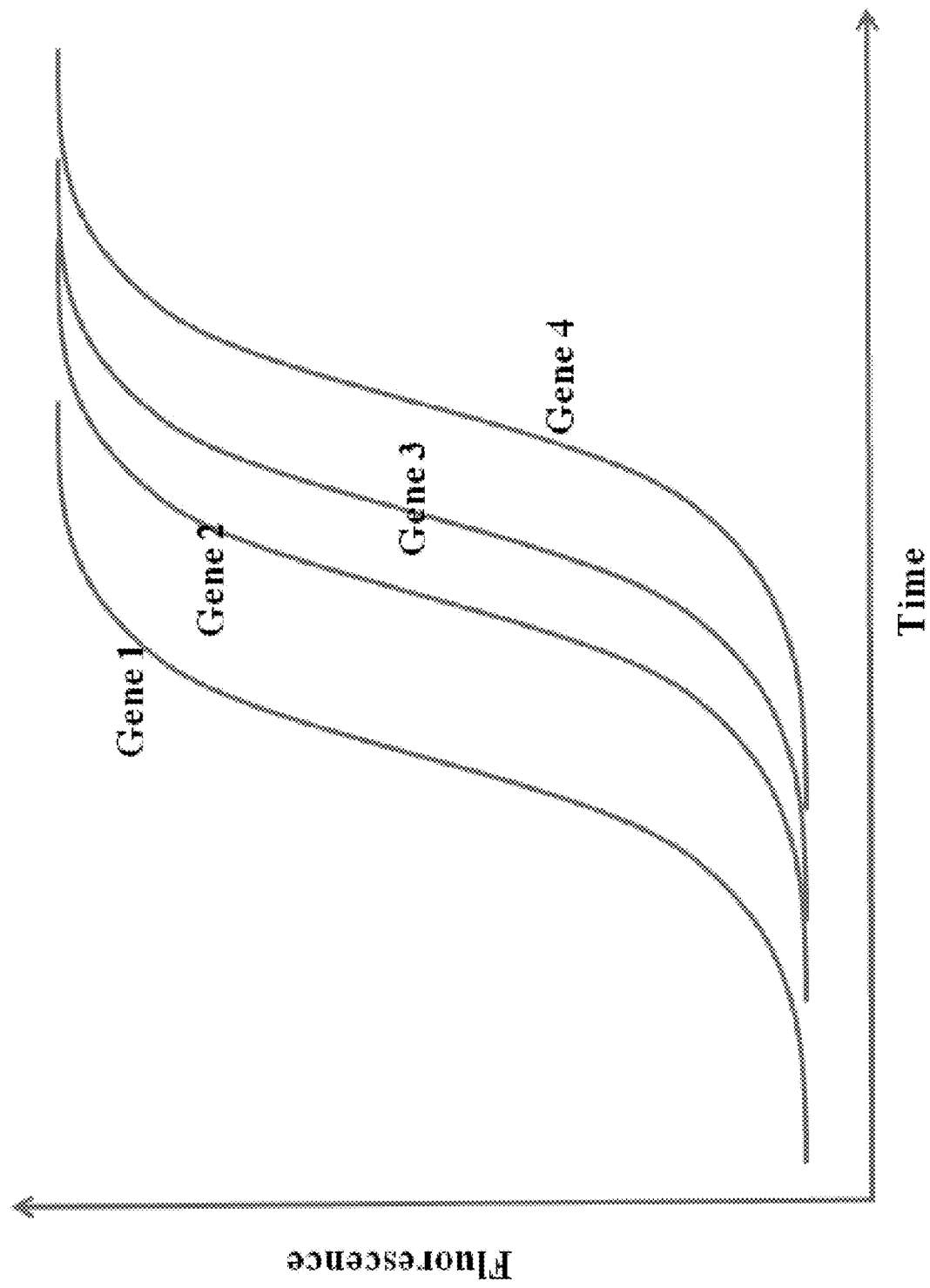
FIG. 5. dPCR amplification curves of four genes with different Ct values.

In one embodiment, the PCR amplification for each target sequence has different threshold cycle numbers (Ct) and the detection of a target sequence is based on the Ct. Because of the difference in PCR efficiency using different primers, different target sequences can have different Ct, which can be used to discriminate target sequences (FIG. 5).

In some embodiment, the detection of a target sequence is based on the plateau fluorescence intensity and the Ct of the amplification curve of the target sequence.

In some embodiment, the mixture of the sample and PCR reagents is partitioned into many small individual reaction volumes such that more than 50% of the reaction volumes contain no more than one nucleic acid sequence. In some embodiment, each reaction volume practically has no more than one single nucleic sequence.

In one embodiment, the present invention provides a method for counting circulating tumor cells expressing a tumor-specific gene or having a tumor-specific genomic sequence in a cell sample using a device described herein, comprising: a) partitioning a mixture of RT-PCR reagents and a cell sample enriched with circulating tumor cells into many small individual reaction volumes in the PCR microchip such that more than 50% of the reaction volumes contain no more than one circulating tumor cell, wherein the mixture comprises tumor-specific primers for amplification of a plurality of tumor-specific sequences and a plurality of sequence-specific reporter probes for detection of the plurality of tumor-specific sequences; b) performing multiplexed real-time quantitative RT-PCR to amplify the plurality of tumor-specific sequences in each reaction volume; c) recording an amplification curve for each reaction volume during the PCR amplification; d) counting the number of reaction volumes with positive fluorescent signals based on the amplification curve of the reaction volume; and e) determining the fraction of circulating tumor cells in the cell sample based on the fraction of reaction volumes with positive fluorescent signals.

Samples used for detection of circulating tumor cells are usually blood cell samples. The blood cell samples can be enriched for circulating tumor cells by removing red blood cells and white blood cells, or by size selection for large tumor cells. The circulating tumor cells are identified by the expression of tumor-specific genes or containing tumor-specific genomic sequence (e.g. tumor-specific mutations). The tumor-specific primers are designed to amplify tumor-specific RNA transcripts using RT-PCR and to amplify tumor-specific DNA sequences using PCR. The preferable tumor-specific sequences are RNA transcripts only expressed in tumor cells or tumor-specific DNA mutations that are not present in normal blood cells. The reaction volumes with positive fluorescent signals are identified as reaction volumes containing a circulating tumor cell.

In some embodiment, different concentrations of the tumor-specific primers and the sequence-specific reporters are used for different tumor-specific sequences which results in different plateau fluorescence intensities for different tumor-specific sequences, and the detection of a circulating tumor cell having a particular tumor-specific sequence is based on the plateau fluorescence intensity.

In some embodiment, the PCR amplification for different tumor-specific sequences has different Ct and the detection of a circulating tumor cell having a particular tumor-specific sequence is based on the Ct.

In some embodiment, the detection of a circulating tumor cell having a particular tumor-specific sequence is based on the plateau fluorescence intensity and the Ct.

In some embodiment, the mixture of PCR reagents and the cell sample is partitioned into many small individual reaction volumes in the PCR microchip such that more than 50% of the reaction volumes contain no more than one single cell.

In some embodiment, the reaction volumes identified as having circulating tumor cells can be retrieved and used for further analysis. For example, the microdroplets having fluorescent signals can be sorted by a droplet sorter and the microdroplets with fluorescent signals are identified with ones with circulating tumor cells.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A device for performing real-time digital PCR, comprising:
    a) more than one PCR mini-reactor wherein the PCR mini-reactor comprises a digital PCR microchip thermally coupled to a temperature control element, wherein the thermal cycle of each PCR mini-reactor is independently controlled by its respective temperature control element, wherein the digital PCR microchip comprises more than 10000 chambers, wherein a nucleic acid sample is partitioned into the chambers to perform the real-time digital PCR and wherein the positive result of each chamber is determined based on the kinetic properties of its amplification curve;
    b) a detection unit wherein the detection unit can be programmed to take images of digital PCR microchips at pre-defined time intervals;
    c) a motor that can be programmed to move PCR mini-reactors or the detection unit to the desired position for taking an image of a digital PCR microchip; and
    d) a computing unit for controlling the coordinated operation of the detection unit, the PCR mini-reactors, the motor, and the temperature control element of each PCR mini-reactor.

2. The device of claim 1, wherein the temperature control element comprises a heating element, a temperature sensor and a cooling element.

3. The device of claim 1, wherein the temperature control element comprises an actuatable top heater integrated with top temperature sensors and a bottom heater integrated with bottom temperature sensors and cooling fins.

4. A device for performing real-time digital PCR, comprising:
    a) more than one PCR mini-reactor wherein the PCR mini-reactor comprises a digital PCR microchip thermally coupled to a temperature control element, wherein the thermal cycle of each PCR mini-reactor is independently controlled by its respective temperature control element, wherein the temperature control element comprises an actuatable top heater integrated with top temperature sensors and a bottom heater integrated with bottom temperature sensors and cooling fins, wherein the digital PCR microchip comprises more than 10000 micro-chambers wherein a nucleic acid sample is partitioned into the micro-chambers to perform the real-time digital PCR and wherein the positive result of each chamber is determined based on the kinetic properties of its amplification curve;
    b) a detection unit wherein the detection unit can be programmed to take images of digital PCR microchips at pre-defined time intervals, wherein the actuatable top heater can be programmed to be moved out of the way to allow the detection unit to take an image;
    c) a motor that can be programmed to move PCR mini-reactors or the detection unit to the desired position for taking an image of a digital PCR microchip; and
    d) a computing unit for controlling the coordinated operation of the detection unit, the PCR mini-reactors, the motor, and the temperature control element of each PCR mini-reactor.

5. The device of claim 1, wherein images of the same digital PCR microchip are aligned by finding similar features of the images and applying homography techniques to align the features.

6. The device of claim 1, wherein the detection unit comprises a light source, optical filters, a fluorescence microscope and a camera.

7. The device of claim 6, wherein the fluorescence microscope is a high resolution wide-field microscope.

8. The device of claim 4, wherein the motor is programmed to move the detection unit to the desired position to take an image of a digital PCR microchip.

9. The device of claim 4, wherein images of the same digital PCR microchip are aligned by finding similar features of the images and applying homography techniques to align the features.

\* \* \* \* \*